US010034599B2

(12) United States Patent
Koshika

(10) Patent No.: US 10,034,599 B2
(45) Date of Patent: Jul. 31, 2018

(54) SCANNING ENDOSCOPE APPARATUS WITH SCANNING ENDOSCOPE AND DETERMINATION CIRCUIT FOR DETERMINING WHETHER SCANNING ENDOSCOPE IS ABNORMAL

(71) Applicant: OLYMPUS CORPORATION, Tokyo (JP)

(72) Inventor: Soichiro Koshika, Mitaka (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/356,542

(22) Filed: Nov. 19, 2016

(65) Prior Publication Data

US 2017/0065154 A1    Mar. 9, 2017

Related U.S. Application Data

(63) Continuation of application No. PCT/JP2015/074727, filed on Aug. 31, 2015.

(30) Foreign Application Priority Data

Jan. 20, 2015 (JP) ................................ 2015-008861

(51) Int. Cl.
*A61B 1/07* (2006.01)
*A61B 1/00* (2006.01)
(Continued)

(52) U.S. Cl.
CPC ............ *A61B 1/00096* (2013.01); *A61B 1/00* (2013.01); *A61B 1/00006* (2013.01);
(Continued)

(58) Field of Classification Search
CPC ... A61B 1/00172; A61B 1/00096; A61B 1/00; A61B 1/00006; A61B 1/0669; A61B 1/07; A61B 1/06; G02B 23/24
See application file for complete search history.

(56) References Cited

U.S. PATENT DOCUMENTS 5,001,649 A * 3/1991 Lo ....................... A61F 9/00745
310/316.01
5,061,882 A * 10/1991 Takagi ..................... H02N 2/14
310/316.02
(Continued)

FOREIGN PATENT DOCUMENTS

| JP | 2014-036779 A | 2/2014 |
| JP | 2014-145942 A | 8/2014 |
| JP | 2014-188221 A | 10/2014 |

OTHER PUBLICATIONS

International Search Report dated Nov. 17, 2015 issued in PCT/JP2015/074727.
(Continued)

*Primary Examiner* — John P Leubecker
(74) *Attorney, Agent, or Firm* — Scully, Scott, Murphy & Presser, P.C.

(57) ABSTRACT

A scanning endoscope apparatus is provided that includes: an endoscope having a light guide portion configured to guide and emit an illuminating light for illuminating a subject, and an actuator configured to oscillate the light guide portion; a storage portion configured to store a resonance frequency at a time when the light guide portion is caused to oscillate in a resonant state; an application portion configured to sequentially apply a plurality of signals having different frequencies to the actuator; a signal monitoring portion configured to monitor signals that are applied to the actuator; and a determination portion configured to compare a frequency of a signal which is smallest in a case where the (Continued)

actuator is taken as a load with the resonance frequency stored in the storage portion to determine whether or not the endoscope is abnormal.

17 Claims, 9 Drawing Sheets

(51) Int. Cl.
*G02B 23/24* (2006.01)
*A61B 1/06* (2006.01)

(52) U.S. Cl.
CPC ........ *A61B 1/00172* (2013.01); *A61B 1/0669* (2013.01); *A61B 1/07* (2013.01); *G02B 23/24* (2013.01)

(56) References Cited

U.S. PATENT DOCUMENTS

| | | | |
|---|---|---|---|
| 6,819,027 B2* | 11/2004 | Saraf | B06B 1/0261 310/316.01 |
| 6,845,190 B1 | 1/2005 | Smithwick et al. | |
| 7,298,938 B2* | 11/2007 | Johnston | A61B 1/0008 385/15 |
| 2002/0049463 A1* | 4/2002 | Friedman | A61B 17/320068 606/169 |
| 2003/0015977 A1* | 1/2003 | Lee | B06B 1/0261 318/114 |
| 2007/0133968 A1* | 6/2007 | Kawamura | G02B 7/28 396/79 |
| 2007/0167881 A1* | 7/2007 | Takahashi | A61B 17/320068 601/2 |
| 2009/0026888 A1 | 1/2009 | Melville | |
| 2009/0243431 A1* | 10/2009 | Ohsawa | F04B 43/046 310/317 |
| 2009/0259221 A1* | 10/2009 | Tahara | A61B 17/320092 606/34 |
| 2009/0316116 A1* | 12/2009 | Melville | A61B 1/0008 353/31 |
| 2014/0194693 A1* | 7/2014 | Imaizumi | G02B 26/10 600/180 |
| 2016/0039671 A1* | 2/2016 | Terazawa | C01B 13/115 422/186.07 |

OTHER PUBLICATIONS

Japanese Office Action dated Apr. 19, 2016 issued in Japanese Patent Application No. 2016-507325.
Extended Supplementary European Search Report dated Jan. 5, 2018 in European Patent Application No. 15 87 8849.7.

* cited by examiner

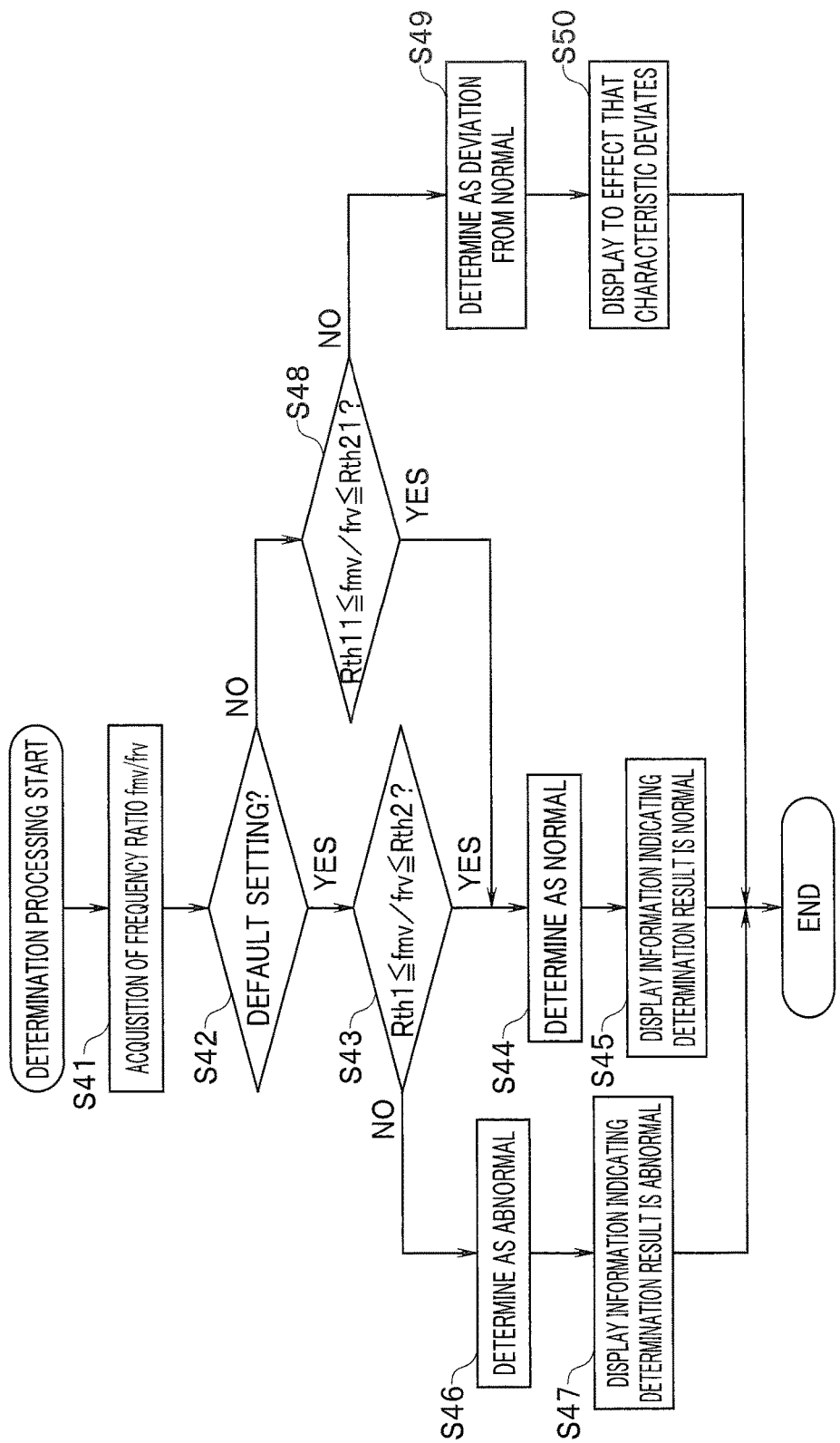

SCANNING ENDOSCOPE APPARATUS WITH SCANNING ENDOSCOPE AND DETERMINATION CIRCUIT FOR DETERMINING WHETHER SCANNING ENDOSCOPE IS ABNORMAL

CROSS REFERENCE TO RELATED APPLICATION

This application is a continuation application of PCT/JP2015/074727 filed on Aug. 31, 2015 and claims benefit of Japanese Application No. 2015-008861 filed in Japan on Jan. 20, 2015, the entire contents of which are incorporated herein by this reference.

BACKGROUND OF THE INVENTION

1. Field of the Invention

The present invention relates to a scanning endoscope apparatus that scans a light that is irradiated at a subject and acquires an endoscopic image.

2. Description of the Related Art

The endoscopes are widely used in the medical field and the like. In recent years, as an endoscope that is inserted inside a subject, a scanning endoscope has been proposed that does not use an image pickup device configured to pick up an image two-dimensionally, and instead two-dimensionally scans a light emitted from a distal end of a light guide portion such as a thin optical fiber and receives reflected light thereof and generates an image.

For example, Japanese Patent Application Laid-Open Publication No. 2014-145942 that is a conventional example discloses a scanning endoscope apparatus which includes: an optical fiber having an oscillation portion whose one end is oscillatably supported; vibration driving means configured to cause the oscillation portion to vibrate based on a driving signal; changing means configured to change a frequency of the driving signal that is sent to the vibration driving means; and a temperature sensor configured to detect a temperature in a vicinity of the oscillation portion; wherein the frequency of the driving signal is changed based on a temperature that the temperature sensor detects, and which is thus configured so that fluctuations in an angle of view relative to changes in the external environment can be suppressed. Further, the aforementioned scanning endoscope apparatus adopts a configuration so that, for example, in a case where the environment changes from an ordinary temperature environment to, for example, a high temperature environment and the angle of view is narrowed due to a decrease in the amplitude of the oscillation portion, fluctuations in the angle of view can be suppressed based on a temperature that is detected by the temperature sensor.

SUMMARY OF THE INVENTION

A scanning endoscope apparatus according to one aspect of the present invention includes: a scanning endoscope having a light guide portion configured to guide an illuminating light for illuminating a subject and emit the illuminating light from an emitting end, and an actuator configured to oscillate the emitting end of the light guide portion in accordance with a voltage of a signal that is applied to the actuator so that the illuminating light scans over the subject; a storage portion configured to store in advance, as information regarding a frequency of the signal that is applied to the actuator, information regarding a resonance frequency when the emitting end of the light guide portion is caused to oscillate in a resonant state; an application portion configured to sequentially apply a plurality of signals having different frequencies to the actuator; a signal monitoring portion configured to monitor the plurality of signals that are sequentially applied to the actuator; and a determination portion configured to compare information regarding a frequency of a signal at a time when impedance is smallest in a case where the actuator is taken as a load among the plurality of signals monitored by the signal monitoring portion with the information regarding the resonance frequency stored in the storage portion to determine whether or not the scanning endoscope is abnormal.

BRIEF DESCRIPTION OF THE DRAWINGS

FIG. 6 is a view illustrating a signal for determination in which a frequency varies that a variable-frequency signal generating circuit generates, and a current that flows through a drive wire which is measured by a current measuring portion and the like;

FIG. 10 is a flowchart illustrating determination processing performed in the alternating operation mode in FIG. 8.

DETAILED DESCRIPTION OF THE PREFERRED EMBODIMENT(S)

Embodiments of the present invention are described hereunder with reference to the drawings.

(First Embodiment)

Figure 1:
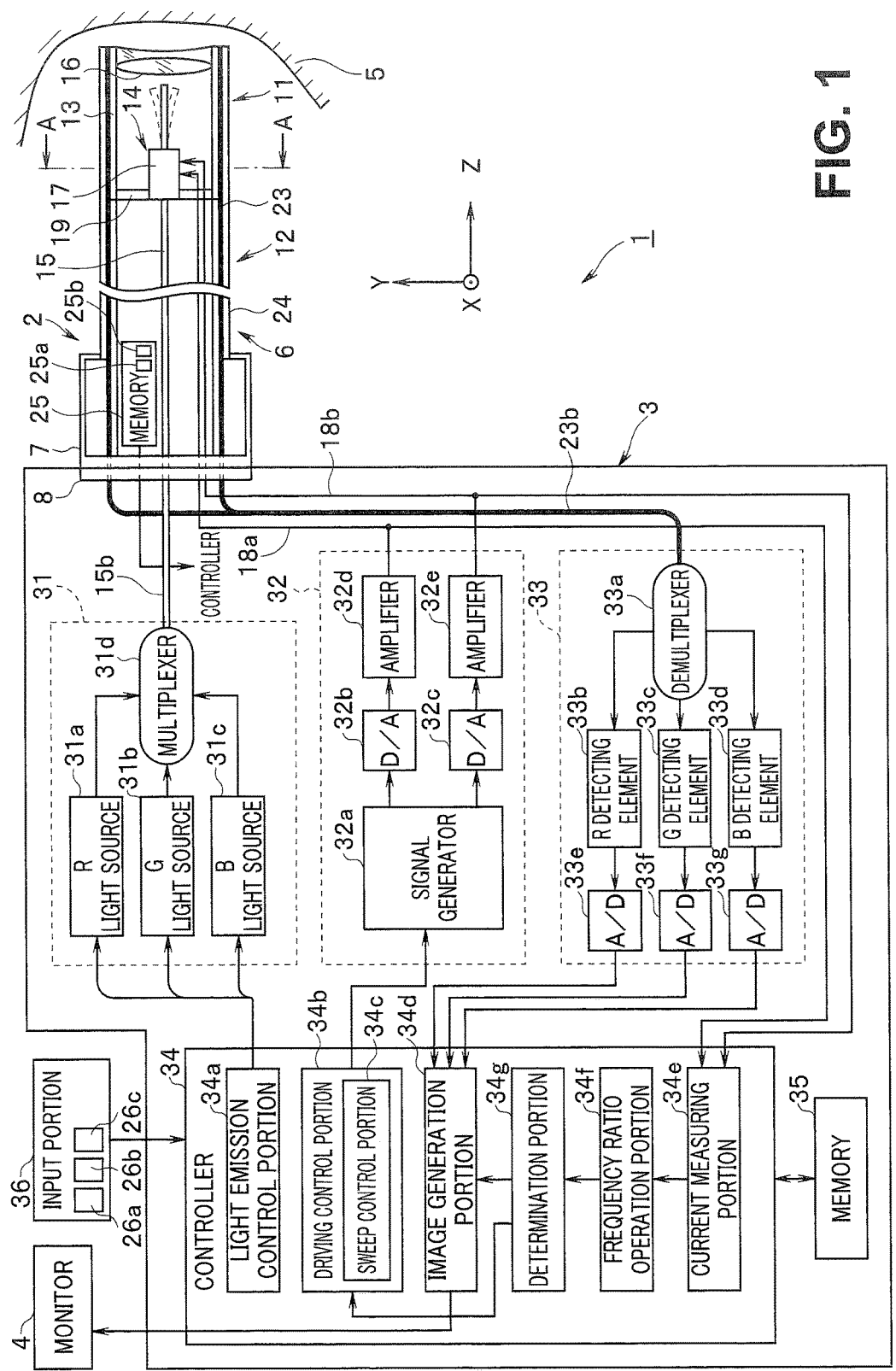
FIG. 1 is a view illustrating an overall configuration of a scanning endoscope apparatus of a first embodiment of the present invention.

A scanning endoscope apparatus 1 of a first embodiment of the present invention that is illustrated in FIG. 1 includes a scanning endoscope 2 forming a scanning optical probe, a main body apparatus (or scanning endoscope control apparatus) 3 to which the scanning endoscope 2 is detachably connected, and a monitor 4 as a display apparatus that is connected to the main body apparatus 3.

The scanning endoscope 2 has an insertion portion 6 which has an elongated shape and is flexible and which is insertable into the body or a body cavity of a subject 5. A connector 7 for detachably connecting the scanning endoscope 2 to a connector receptacle 8 of the main body apparatus 3 is provided at a proximal end (rear end) of the insertion portion 6.

The insertion portion 6 also has a rigid distal end portion 11, and a flexible tube portion 12 that has flexibility and which extends from the rear end of the distal end portion 11 to the connector 7. Note that a configuration may be adopted in which a bendable bending portion is provided between the distal end portion 11 and the flexible tube portion 12, and an operation portion on which operation knobs or the like are provided for bending the bending portion is provided between the flexible tube portion 12 and the connector 7.

The distal end portion 11 has a cylindrical member 13 as a rigid tubular member. A distal end of a flexible cylindrical tube is connected to a rear end of the cylindrical member 13. The connector 7 is fixed to a rear end of the cylindrical tube. Note that a structure in which the cylindrical tube is not provided may also be adopted.

An optical fiber 15 which forms a light guide portion that guides an illuminating light is inserted through the inside of the insertion portion 6. A proximal end (rear end) of the optical fiber 15 is connected at the connector 7 to an optical fiber 15b which is provided inside the main body apparatus 3. An illuminating light that is generated at a light source unit 31 which forms a light source portion inside the main body apparatus 3 passes through the optical fiber 15b and enters a proximal end of the optical fiber 15. The illuminating light that is guided by the optical fiber 15 travels from a distal end face that is an emitting end of the optical fiber 15 via an illumination lens 16 which converges the light that is mounted at a distal end of the cylindrical member 13 and that faces the distal end face, and is emitted toward an examination site that is an observation object inside the subject 5.

An actuator 17 constituting a scanning portion (or scanning unit) 14 that scans a distal end side of the optical fiber 15 so as to oscillate in a direction that is orthogonal to a longitudinal direction (Z-axis direction in FIG. 1) of the optical fiber 15 is disposed inside the cylindrical member 13. Note that the scanning portion 14 is formed by the actuator 17 that holds the optical fiber 15.

The actuator 17 expands and contracts in the longitudinal direction in response to application of driving signals (or driving voltages) to the actuator from a driving unit 32 provided inside the main body apparatus 3 through drive wires 18a and 18b inserted through the inside of the insertion portion 6.

A proximal end of the actuator 17 is held by a holding member 19. A discoid outer circumferential face of the holding member 19 is fixed to an inner face of the cylindrical member 13. The optical fiber 15 and the actuator 17 are bonded together by a ferrule 20 (see FIG. 2) as a bonding member or support member.

Figure 2:
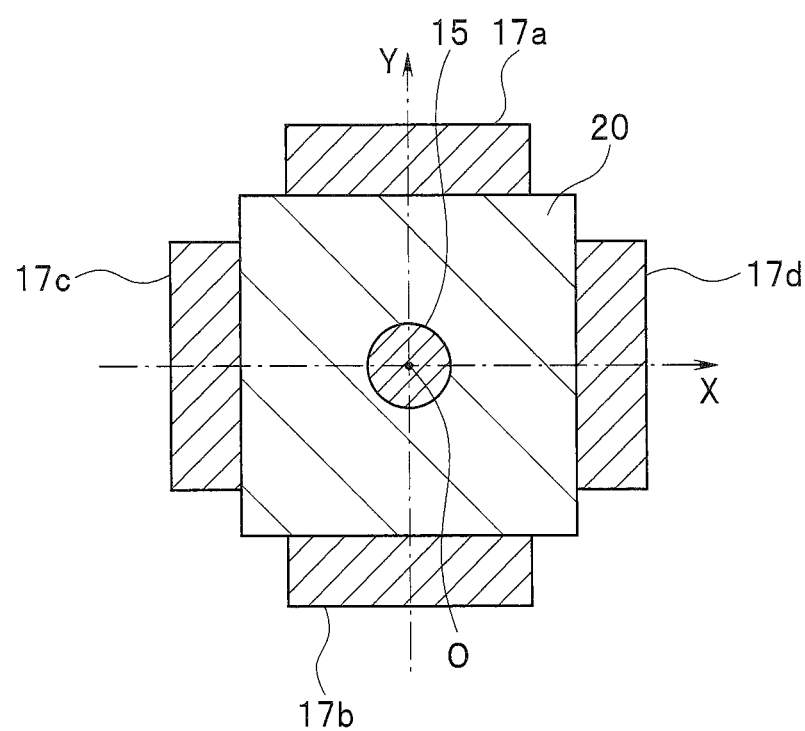
FIG. 2 is a view illustrating a configuration of a peripheral portion of an actuator.

FIG. 2 illustrates the configuration of a peripheral portion of the actuator 17 by means a cross-section along a line A-A in FIG. 1. The ferrule 20 as a rigid bonding member of a rectangular parallelepiped shape which is square in cross section that is disposed along a central axis O (in the cylindrical member 13) as shown in FIG. 2 is formed of, for example, zirconia (ceramic) or nickel.

The optical fiber 15 is fixed along the central axis O by the ferrule 20. Further, actuator elements 17a and 17b, and 17c and 17d that form the actuator 17 are attached to both side faces in the Y-axis direction (upward-downward or vertical direction on the paper surface) that is orthogonal to the Z-axis, and to both side faces in the X-axis direction (lateral or horizontal direction on the paper surface), respectively.

Each actuator element is, for example, constituted by a piezoelectric element, and is configured to expand and contract in a longitudinal direction (Z-axis direction in FIG. 1) upon application of a driving signal to electrodes (omitted from the illustration) on both sides of the piezoelectric element. Therefore, in a state in which the proximal end of the optical fiber 15 is held or fixed, the distal end side of the optical fiber 15 can be caused to oscillate in the vertical direction as indicated by dashed lines in FIG. 1 by application of, for example, driving signals (or driving voltages) through the drive wire 18a to the actuator elements 17a and 17b (to expand one of the actuator elements and contract the other). Note that, in FIG. 1, a configuration is illustrated in which output signals of the amplifiers 32d and 32e are applied to (the actuator elements 17a and 17b and the actuator elements 17c and 17d foaming) the actuator 17 through the drive wires 18a and 18b, and at least in a determination mode that is described later, currents flowing through the drive wires 18a and 18b are measured by a current measuring portion 34e (see FIG. 5).

Further, the holding member 19 is fitted to an inner face of the proximal end of the cylindrical member 13 and is fixed to the inner face by adhesive or the like.

Figure 3:
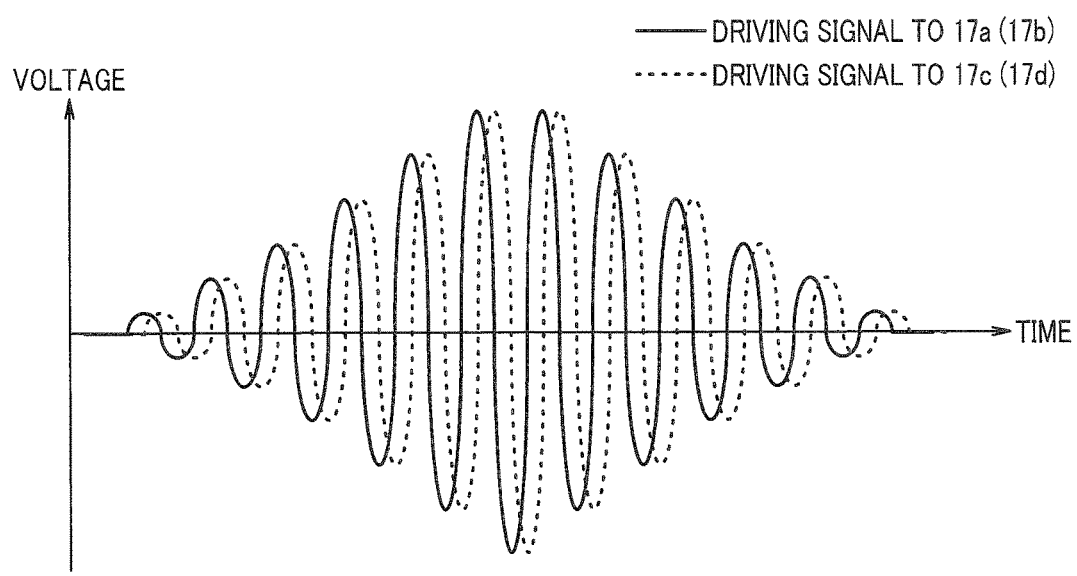
FIG. 3 is a view illustrating waveforms of driving signals applied to actuator elements constituting the actuator.
Figure 4:
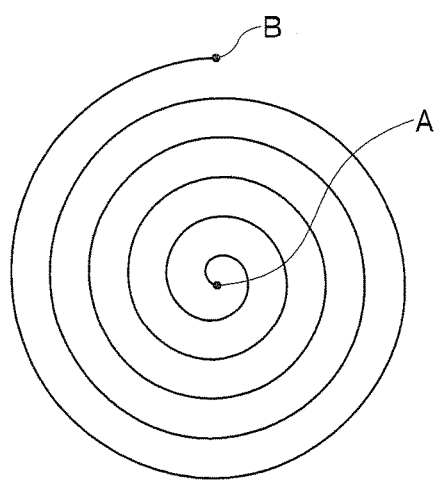
FIG. 4 is a view illustrating a spiral trajectory that is traced by an illuminating light emitted from a distal end of an optical fiber in the case illustrated in FIG. 3.

FIG. 3 illustrates voltage waveforms of driving signals applied to the actuator elements 17a and 17b and the actuator elements 17c and 17d, based on which the distal end of the optical fiber 15 traces a spiral path (or trajectory) as shown in FIG. 4. As shown in FIG. 3, by applying driving signals for driving in the X-axis direction and the Y-axis direction to the actuator elements 17a and 17b and the actuator elements 17c and 17d in a state in which the phases of the driving signals are shifted by 90° relative to each other and changing the voltages little by little over time, the distal end of the optical fiber 15 traces a spiral trajectory from a circular shape. Note that, although in the present embodiment the actuator 17 is formed using the actuator elements 17a and 17b, and the actuator elements 17c and 17d that are respective pairs of actuator elements so as to cause the distal end of the optical fiber 15 to oscillate (vibrate) in two orthogonal directions, the present invention can also be applied to a case in which the actuator 17 is formed using a single actuator element instead of the pairs of actuator elements, respectively (for example, 17a and 17c).

As shown in FIG. 1, a plurality of light-receiving optical fiber bundles (abbreviated as "light-receiving optical fibers") 23 for receiving illuminating light reflected on the examination site side of the subject 5 are disposed in a ring shape along an outer circumferential face of the cylindrical member 13 and the cylindrical tube. Light (return light or reflected light from the examination site side) received by the light-receiving optical fibers 23 is guided to a light-receiving optical fiber 23b inside the main body apparatus 3 via the connector 7. The light that is guided to the light-receiving optical fiber 23b enters a detection unit 33 and is converted to an electrical signal.

The light-receiving optical fibers 23 that are disposed in a ring shape are covered and protected by a flexible exterior member 24.

Each scanning endoscope 2 has a memory 25 that stores information such as driving data for driving the distal end of the optical fiber 15 along a predetermined scanning pattern that has a spiral shape by means of the actuator 17 and coordinate position data corresponding to irradiation positions (scanning positions or scanning spot positions) at times when the distal end of the optical fiber 15 is driven. The information stored in the memory 25 is inputted to a controller 34 inside the main body apparatus 3 via a contact of the connector 7 and a signal wire. The controller 34 stores the aforementioned inputted information in a memory 35, for example, and refers to the information stored in the memory 35 to control the light source unit 31 and the driving unit 32.

Further, in the present embodiment, for example, information on resonance frequencies that is acquired in advance by driving the actuator 17 which is mounted in respective scanning endoscopes 2 in a state in which normal operation is performed at a time of factory shipment or the like is stored in the memory 25.

That is, one part of the storage area in the memory 25 forms a frequency information storage portion 25a that stores resonance frequency information (which is acquired in advance in a normal operating state). As described later, the resonance frequency information is referred to when an operation in a determination mode is performed, and is utilized when a determination is made as to whether or not (the scanning portion 14 including the actuator 17 mounted in) the scanning endoscope 2 is abnormal. The memory 25 also stores information on threshold values for determining, based on a change in a resonance frequency, that the operating state has changed from a normal operating state to an abnormal operating state due to a change in a characteristic of the scanning portion 14 provided inside the distal end portion 11 as a result of the distal end portion 11 deforming or the like. That is, the memory 25 has a function of a threshold value storage portion (or threshold value information storage portion) 25b that stores information on threshold values for abnormality determination.

Note that because the actuator 17 is constituted by the actuator elements 17a and 17b, and the actuator elements 17c and 17d that are caused to vibrate in two directions which are orthogonal to each other as described above, the frequency information storage portion 25a stores a resonance frequency frv for a case where the actuator elements 17a and 17b are caused to vibrate in the vertical direction and a resonance frequency frh for a case where the actuator elements 17c and 17d are caused to vibrate in the horizontal direction.

Furthermore, with respect to the two resonance frequencies frv and frh, the threshold value information storage portion 25b stores threshold values for abnormality determination for a case where the respective values deviate to a low frequency side, and threshold values for abnormality determination for a case where the respective values deviate to a high frequency side.

Note that, because the actuator elements 17a and 17b and the actuator elements 17c and 17d whose characteristics are uniform are used, the resonance frequencies frv and frh are approximately the same frequency within a range of an allowed small frequency difference. In a case where the frequency difference can be ignored, a configuration may be adopted in which, for example, a single resonance frequency fr (=(frv+frh)/2) that is the average value of the two resonance frequencies frv and frh is stored, and a determination as to whether or not there is an abnormality is made using the single resonance frequency fr. Further, with respect to the threshold values for abnormality determination also, a configuration may be adopted in which a common threshold value for abnormality determination is used for the two resonance frequencies frv and frh.

The main body apparatus 3 includes the light source unit 31, the driving unit 32, the detection unit 33, the controller 34 configured to control each unit of the main body apparatus 3, and the memory 35 that is connected to the controller 34 and stores various kinds of information. An input portion (or input unit) 36 which a user uses to input various instructions is also connected to the controller 34 of the main body apparatus 3. The input portion 36 is constituted by a keyboard or a mouse or the like.

In the present embodiment, a mode switching switch 26a that is configured to perform mode switching to switch between an observation mode that acquires an endoscopic image as a normal observation image for observing an examination site and a determination mode that performs a determination as to whether the scanning endoscope 2 is normal or abnormal, and an alternating operation mode switch 26b that is configured to issue an instruction in the observation mode so as to alternately perform operation in the observation mode and operation in the determination mode are provided in the input portion 36. Instruction signals from these switches 26a and 26b are inputted to (a driving control portion 34b or the like inside) the controller 34. The switching switch 26a has a function of a mode switching portion that switches between an observation mode that acquires an observation image of the subject 5 by means of the scanning endoscope 2, and a determination mode that determines an abnormality of the scanning endoscope 2. In this case, a portion that includes, in addition to the switching switch 26a that generates an instruction signal, the controller 34 that performs control operations to switch between the observation mode and the determination mode in accordance with the instruction signal may be defined as having a function of a mode switching portion.

The alternating operation mode switch 26b also has a function of a switching portion configured to alternately switch between the observation mode in which a signal of a prescribed frequency is applied to the actuator 17 to obtain an observation image of the subject 5 by means of the scanning endoscope 2 and the determination mode in which a plurality of signals of different frequencies are sequentially applied (in other words, signals whose frequencies are varied are applied) to the actuator 17 to determine an abnormality of the scanning endoscope 2. In this case also, a portion that includes the controller 34 in addition to the alternating operation mode switch 26b may be defined as having a function of a switching portion that alternately switches between the observation mode and the determination mode.

A parameter selection switch 26c is also provided in the input portion 36. The parameter selection switch 26c is configured to, with respect to the determination mode that is (alternately) operated in the alternating operation mode by the alternating operation mode switch 26b, select a parameter of a frequency variation range in a case where a frequency is varied or of a threshold value relating to the corresponding determination processing.

For example, in default settings which are preset, a sweep parameter is set so as to generate a signal for sweeping, in a short time period, a frequency variation range that is the same as in a case of the determination mode that is performed in an initial state, and in this case a threshold value parameter that is the same as in the initial state is adopted. According to this default setting, it is possible to make a determination as to whether or not there is an abnormality in a short time period, even though the accuracy of the determination result is not as high as when a longer time period is taken as in the case of the initial state.

In contrast, the parameter selection switch 26c can be used to select a parameter so as to sweep a narrower frequency variation range than the aforementioned frequency variation range.

In this case, a parameter is set so as to generate signals in a frequency range in the vicinity of resonance frequencies stored in the frequency information storage portion 25a that is a frequency range which includes such resonance frequencies.

Further, in correspondence to the setting of this parameter, a parameter of a threshold value for determining a change in state from a normal state to a state that is partway between the normal state and an abnormal state is set.

In this case, a determination is made as to whether or not a characteristic of the actuator 17 changed to a characteristic that deviates from a normal state.

The light source unit 31 has an R light source 31a configured to generate light in the red wavelength band (hereinafter also referred to as "R light"), a G light source 31b configured to generate light in the green wavelength band (hereinafter also referred to as "G light"), a B light source 31c configured to generate light in the blue wavelength band (hereinafter also referred to as "B light"), and a multiplexer 31d configured to multiplex (mix) the R light, G light and B light. Although light emission by the light source unit 31 is turned on/off as described below in the observation mode, in the determination mode the light source unit 31 is set to be always off (state in which light is not emitted).

The R light source 31a, G light source 31b and B light source 31c are constituted using, for example, laser light sources, and in the observation mode emit the R light, the G light and the B light to the multiplexer 31d, respectively, when turned on by the control by the controller 34. The controller 34 includes a light emission control portion (or light emission control circuit) 34a constituted by a central processing unit (abbreviated as "CPU") or the like that is configured to control pulsed light emission of the R light source 31a, the G light source 31b and the B light source 31c.

The light emission control portion 34a that performs light emission control with respect to the R light source 31a, the G light source 31b and the B light source 31c has a function of an emission control portion configured to control emission of an illuminating light in order to, in a case where the R light sources 31a, the G light source 31b and the B light source 31c are caused to emit light, cause (illuminating light of) the R light, the G light and the B light to be emitted to the side of the observation site from the emitting end of the optical fiber 15 via the illumination lens 16.

The light emission control portion 34a of the controller 34 transmits control signals for simultaneous and pulsed light emission to the R light source 31a, the G light source 31b, and the B light source 31c, and the R light source 31a, the G light source 31b, and the B light source 31c simultaneously generate the R light, the G light, and the B light and emit the R light, the G light, and the B light to the multiplexer 31d.

The multiplexer 31d multiplexes the R light from the R light source 31a, the G light from the light source 31b, and the B light from the light source 31c and supplies the light to a light incident face of the optical fiber 15b. The optical fiber 15b supplies the multiplexed R light, G light, and B light as illuminating light to the optical fiber 15. As described above, in the determination mode the light emission control portion 34a controls so that the light source unit 31 does not emit light or so that the light source unit 31 does not emit an illuminating light.

The driving unit 32 has a signal generator 32a configured to generate digital alternating current signals that are close to a sine wave. Digital alternating current signals that are outputted from two output terminals of the signal generator 32a are inputted to two D/A converters 32b and 32c. Two analog alternating current signals obtained by conversion by the two D/A converters 32b and 32c are amplified by the amplifiers 32d and 32e, respectively, and serve as two driving signals that are applied through the drive wires 18a and 18b to the actuator elements 17a and 17b and the actuator elements 17c and 17d, respectively.

Note that, as described hereunder, in the present embodiment, during operation in the determination mode a driving signal (referred to as "signal for determination") for determining an abnormality is applied to one pair of actuator elements among the actuator elements 17a and 17b that are caused to vibrate (oscillate) in the vertical direction and the actuator elements 17c and 17d that are caused to vibrate (oscillate) in the lateral direction, and after application of a signal for determination for determining an abnormality by applying a signal for determination to the one pair of actuator elements ends, application of a signal for determination for determining an abnormality is performed with respect to the other pair of actuator elements.

Figure 5:
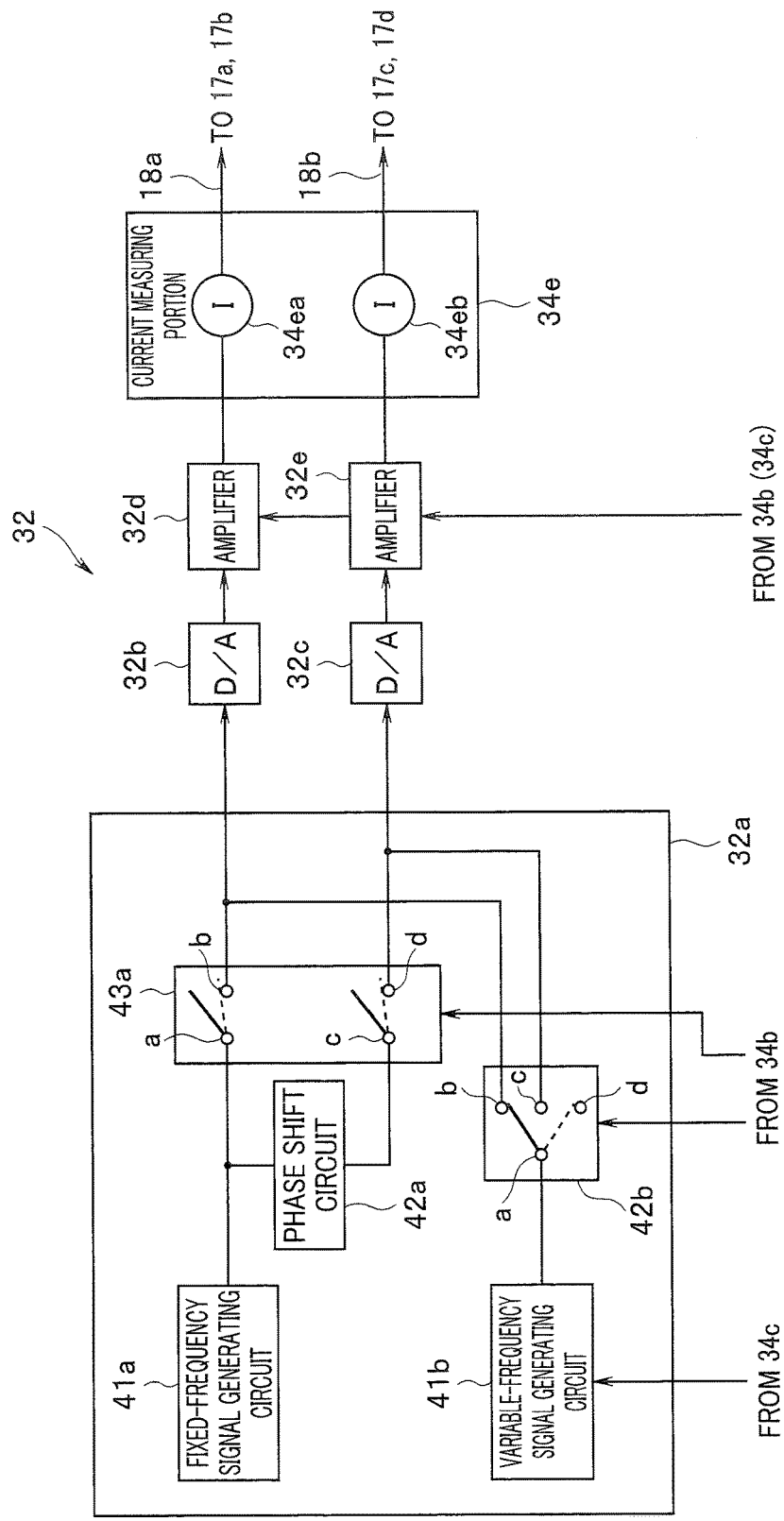
FIG. 5 is a circuit diagram illustrating one configuration example of a signal generator.

FIG. 5 illustrates a configuration example of the signal generator 32a.

The signal generator 32a has a fixed-frequency signal generating circuit 41a that corresponds to the observation mode, and a variable-frequency signal generating circuit 41b that corresponds to the determination mode. The fixed-frequency signal generating circuit 41a generates a digital alternating current signal of a prescribed frequency that is a fixed frequency, and the digital alternating current signal is outputted to a phase shift circuit 42a and a contact point a of a switching circuit 43a.

The phase shift circuit 42a generates a digital alternating current signal having a phase difference of 90° relative to the inputted digital alternating current signal, and outputs the digital alternating current signal having the phase difference of 90° to a contact c of the switching circuit 43a. A contact b that turns on/off with the contact a, and a contact d that turns on/off with the contact c of the switching circuit 43a serve as first and second output terminals in the signal generator 32a, and are connected to input terminals of the D/A converters 32b and 32c shown in FIG. 2, respectively.

On the other hand, a digital alternating current signal in which the frequency varies that is generated at the variable-frequency signal generating circuit 41b is inputted to a common contact a of a switching switch circuit 42b. Contacts b and c that turn on selectively with the common contact a are connected to first and second output terminals, respectively. Note that a contact d is a contact that is not connected to either of the contacts.

In the switching circuit 43a and the switching switch circuit 42b, turning on/off and switching of contacts are controlled by driving control signals from the driving control portion (or driving control circuit) 34b of the controller 34. In the case of the observation mode, the driving control portion 34b places the contacts a and b in the switching circuit 43a in an "on" state as indicated by a dashed line, and also places the contacts c and d in an "on" state, and switches the common contact a in the switching switch circuit 42b so as to select the contact d as indicated by a dashed line.

In the case of the determination mode, the driving control portion 34b switches the switching circuit 43a and the switching switch circuit 42b as indicated by the solid lines. However, with respect to the switching switch circuit 42b, the driving control portion 34b switches so that the common contact a turns the contacts b and c on alternately.

Figure 6:
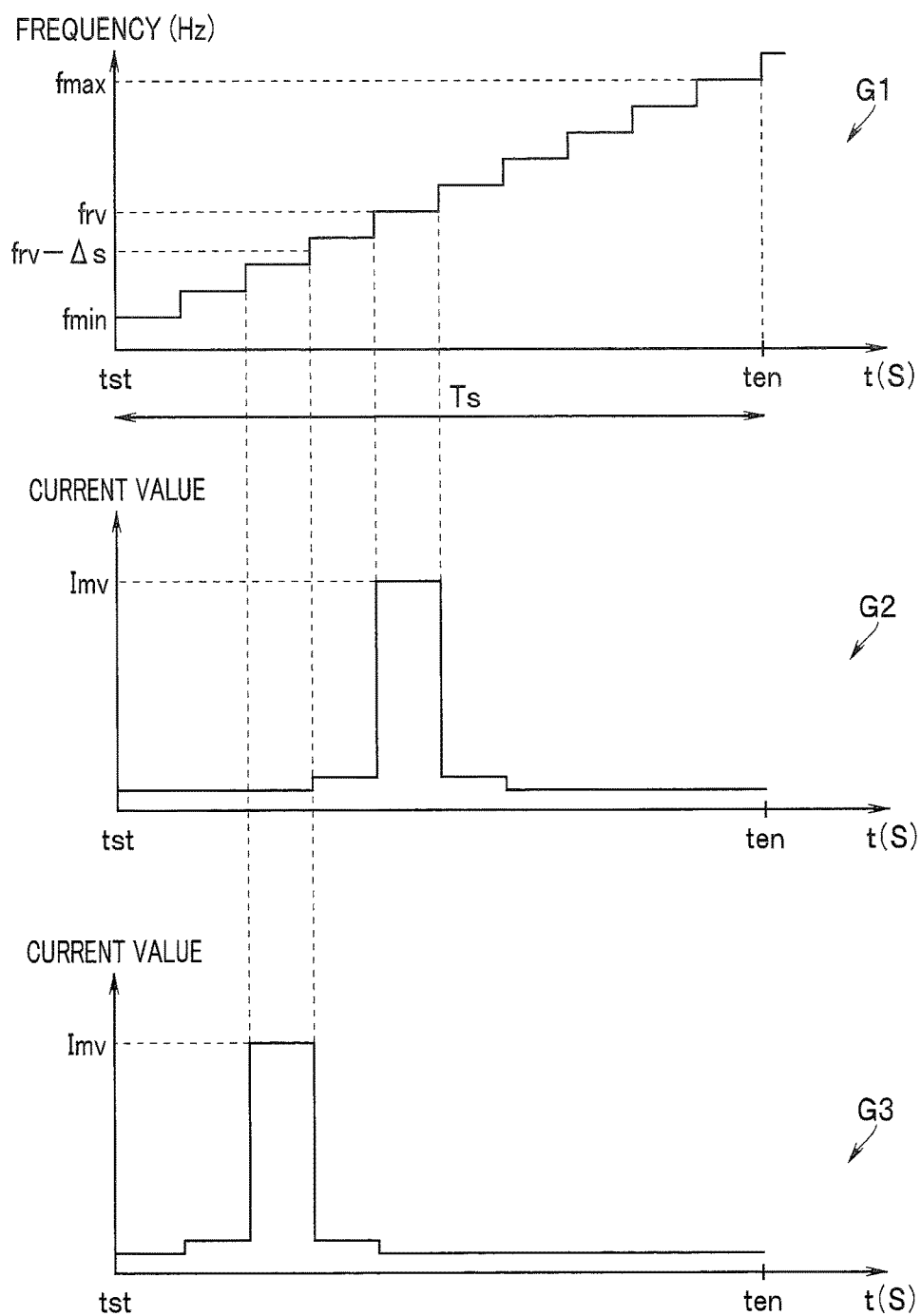

Further, in the case of the determination mode, a sweep control portion (or a sweep control circuit) 34c inside the driving control portion 34b controls so that the variable-frequency signal generating circuit 41b generates alternating current signals in which the frequency varies so as to increase gradually from a lower limit frequency fmin to an upper limit frequency fmax. In FIG. 6, a graph denoted by reference character G1 illustrates the manner in which the frequency changes in an alternating current signal that changes over time which is generated by the variable-frequency signal generating circuit 41b. The signal generating circuit 41b sweeps the alternating current signal from the frequency fmin to the frequency fmax over a predetermined time period (a time period Ts from tst to ten in G1 in FIG. 6). Note that a configuration may also be adopted in which the value of the stepwise frequency variation amount shown in G1 in FIG. 6 is made smaller to thereby set a characteristic that is close to a continuous change. Further, as shown in FIG. 5, after passing through (current measurement circuits 34ea and 34eb forming) the current measuring portion 34e, output signals of the amplifiers 32d and 32e are applied through the drive wires 18a and 18b to the actuator elements 17a and 17b and the actuator elements 17c and 17d. The current measurement circuits 34ea and 34eb are configured to measure currents flowing through the respective drive wires 18a and 18b to the actuator elements 17a and 17b and the actuator elements 17c and 17d, respectively. Note that, because current measurement is not performed in the observation mode, a configuration may be adopted in which an unshown switching circuit or the like is provided and (the current measurement circuits 34ea and 34eb of) the current measuring portion 34e are interposed partway along the drive wires 18a and 18b as shown in FIG. 5 only for a case of performing operation in the determination mode. The present invention is not limited to a case of using the two current measurement circuits 34ea and 34eb, and for example a configuration may also be adopted in which a single current measurement circuit is provided, and the current measurement circuit is interposed partway along a drive wire in which a current is to be actually measured in the case of the determination mode.

Note that the range between the lower limit frequency fmin and the upper limit frequency fmax that is the frequency range of alternating current signals that the variable-frequency signal generating circuit 41b generates is set so as to include the resonance frequencies frv and frh that are stored in the aforementioned frequency information storage portion 25a. For example, taking $\Delta 1$ and $\Delta 2$ as positive values, the frequencies fmin and fmax may be set as fmin=frv$-\Delta 1$ and fmax=frv$+\Delta 2$. Further, $\Delta 1$ and $\Delta 2$ may be set to the same value.

With respect to the resonance frequency frh also, the frequencies fmin and fmax may be set so as to satisfy approximately the same relation as that with the resonance frequency frv. Further, the aforementioned frequencies fmin to fmax (in other words, frv$-\Delta 1$ to frv$+\Delta 2$) are set so as to include a lower limit-side frequency and an upper limit-side frequency for abnormality determination.

Although in the example schematically illustrated in G1 in FIG. 6, a case is illustrated in which a lower limit-side deviation amount As for abnormality determination is set (as a threshold value) partway between the resonance frequency frv and the lower limit frequency fmin, an upper limit-side deviation amount (not shown in the drawing) for abnormality determination is also similarly set partway between the resonance frequency frv and the upper limit frequency fmax. Furthermore, with regard to the resonance frequency frh also, a lower limit-side deviation amount and an upper limit-side deviation amount are similarly set.

By the driving control portion 34b switching in accordance with operations in the observation mode and the determination mode as described above, in the case of the observation mode the fixed-frequency signal generating circuit 41a of the signal generator 32a outputs two digital alternating current signals which have a prescribed frequency and whose phases differ from each other by 90° to the D/A converters 32b and 32c, and after passing through the D/A converters 32b and 32c and being amplified by the amplifiers 32d and 32e, respectively, the resultant driving signals are applied to the actuator elements 17a and 17b and the actuator elements 17c and 17d.

On the other hand, in the case of the determination mode, the variable-frequency signal generating circuit 41b of the signal generator 32a sequentially outputs digital alternating current signals in which the frequencies vary to the D/A converters 32b and 32c. The digital alternating current signal inputted to the D/A converter 32b is converted to an analog alternating current signal by the D/A converter 32b, and the analog alternating current signal is further amplified by the amplifier 32d to become a signal for determination and is applied to the actuator elements 17a and 17b through the drive wire 18a.

Similarly, the digital alternating current signal that is inputted to the D/A converter 32c is converted to an analog alternating current signal by the D/A converter 32c, and the analog alternating current signal is further amplified by the amplifier 32e to become a signal for determination and is applied to the actuator elements 17c and 17d through the drive wire 18b.

Note that, in the case of the determination mode, the driving control portion 34b, for example, controls the gain of the amplifiers 32d and 32e to make the alternating voltage (amplitude) of the signals for determination less than in the case of the observation mode. That is, in the case of the determination mode, the driving control portion 34b controls the alternating voltage (amplitude) of signals for determination that are outputted from the amplifiers 32d and 32e so as to make the alternating voltage (amplitude) less than in the case of the observation mode.

The aforementioned variable-frequency signal generating circuit 41b constitutes an application portion (or application circuit) configured to sequentially apply a plurality of signals of different frequencies to the actuator 17.

In the case of the observation mode, the driving signals outputted from the amplifiers 32d and 32e have the waveforms illustrated in FIG. 3 described above.

The detection unit 33 includes a demultiplexer 33a, detecting elements 33b, 33c and 33d, and A/D converters 33e, 33f and 33g.

The demultiplexer 33a includes a dichroic mirror and the like, and is configured to split return light emitted from the light emission end face of the light-receiving optical fiber 23b into light of the respective color components of R (red), G (green) and B (blue), and to emit the light of the respective color components to the detecting elements 33b, 33c and 33d.

The detecting elements 33b, 33c and 33d are constituted by photodetectors, such as photodiodes, and detect an intensity of the R light, an intensity of the G light, and an intensity of the B light outputted from the demultiplexer 33a, respectively, generate analog R, G, and B detection signals corresponding to the detected intensities of the R light, the G light, and the B light, respectively, and output the signals to the A/D converters 33e, 33f, and 33g.

The A/D converters 33e, 33f, and 33g convert the analog R, G, and B detection signals respectively outputted from the detecting elements 33b, 33c and 33d into digital R, G, and B detection signals, respectively, and output the signals to an image generation portion 41d inside the controller 34. The image generation portion 41d generates an image signal of an observation image corresponding to the scanning position based on the detection signals, and outputs the image signal to the monitor 4 to display the observation image on the monitor 4.

Note that in the present embodiment, as mentioned above, in the determination mode, because control is performed so as not to emit an illuminating light, a configuration may be adopted so as to control the detection unit 33 so as not to actuate the detection unit 33, and to stop a processing operation that generates an observation image based on detection signals in the image generation portion 41d.

Further, the present embodiment includes the current measuring portion (or current measurement circuit) 34e forming a signal monitoring portion (or signal monitoring circuit) that is configured to monitor signals for determination that are applied to the actuator elements 17a and 17b, and the actuator elements 17c and 17d in the determination mode.

In a case where the variable-frequency signal generating circuit 41b generates an alternating current signal in which the frequency is varied, and a signal for determination obtained by amplifying the alternating current signal at the amplifier 32d is applied to the actuator elements 17a and 17b through the drive wire 18a, the current measuring portion 34e measures the current that flows in the drive wire 18a connecting the amplifier 32d and the actuator elements 17a and 17b.

Likewise, in a case where the variable-frequency signal generating circuit 41b generates an alternating current signal in which the frequency is varied, and a signal for determination obtained by amplifying the alternating current signal at the amplifier 32e is applied to the actuator elements 17c and 17d through the drive wire 18b, the current measuring portion 34e measures the current that flows in the drive wire 18b connecting the amplifier 32e and the actuator elements 17c and 17d.

When a signal for determination in which the frequency is varied is applied to the actuator elements 17a and 17b, the current measuring portion 34e acquires a frequency fmv of the signal for determination for which the current flowing through the drive wire 18a is largest. Similarly, when a signal for determination in which the frequency is varied is applied to the actuator elements 17c and 17d, the current measuring portion 34e acquires a frequency fmh (see FIG. 7) of the signal for determination for which the current flowing through the drive wire 18b is largest. Note that, since frequency variation characteristics are known, in a case of measuring a current in synchrony with variations in frequencies, a corresponding frequency can be acquired based on a time when the current is largest.

In a case where a signal for determination in which the frequency is varied is applied to the actuator elements 17a and 17b as described above, the actuator elements 17a and 17b to which the signal for determination is applied are the load to which the signal for determination is applied, and when a frequency of the signal for determination matches a resonance frequency with respect to vibrations in the vertical direction caused by expansion and contraction of the actuator elements 17a and 17b, the actuator elements 17a and 17b and the optical fiber 15 vibrate in a resonant state.

In the resonant state, the actuator elements 17a and 17b (including the optical fiber 15) enter a state in which the (electrical) impedance of the (electrical) load with respect to the signal for determination is smallest.

Further, in the resonant state in which the impedance of the load is smallest, since the current that flows to the actuator elements 17a and 17b (including the optical fiber 15) becomes largest, the current measuring portion 34e measures a current value when the current value is largest, and thus acquires the frequency fmv of the signal for determination at a time when the current value is largest. In FIG. 6, graphs denoted by reference characters G2 and G3 illustrate states (of measurement currents) when, in the case where the frequency is varied as in G1 in FIG. 6, a current flowing through the drive wire 18a is measured in a nomial operating state and in an abnormal operating state.

In the normal operating state illustrated in G2 in FIG. 6, a frequency of a current value Imv at a time when the current is largest almost matches the resonance frequency frv (frv in G1 in FIG. 6) that is stored in the frequency information storage portion 25a. In contrast, in the abnormal operating state illustrated in G3 in FIG. 6, a frequency of the current value Imv at a time when the current is largest deviates from the resonance frequency frv stored in the frequency information storage portion 25a by an amount exceeding a lower limit-side threshold value Δ1 and an upper limit-side threshold value Δ2 for abnormality determination. Although in G1 in FIG. 6 the deviation amount Δs on the lower limit side from the resonance frequency frv is shown as a threshold value for abnormality determination, a configuration may also be adopted in which a threshold value for abnormality determination is set using a frequency ratio with respect to the resonance frequency frv as described below.

The current measuring portion 34e also similarly measures a current value Imh at a time when the current is largest with respect to the actuator elements 17c and 17d that are provided in an orthogonal direction relative to the actuator elements 17a and 17b, and acquires the frequency frh of the signal for determination in a case where the current value Imh is largest.

The information regarding the frequencies fmv and fmh acquired by the current measuring portion 34e is sent to a frequency ratio operation portion (or frequency ratio operation circuit) 34f inside the controller 34. The frequency ratio operation portion 34f performs an operation to calculate a ratio between the received information for the frequencies fmv and fmh and information regarding the resonance frequencies frv and frh stored in the frequency information storage portion 25a, and sends the result of the operation to a determination portion (or determination circuit) 34g.

The determination portion 34g makes a determination as to whether the scanning endoscope 2 is normal or abnormal based on whether or not the frequency ratios fmv/frv and fmh/frh of the acquired frequencies fmv and fmh with respect to the resonance frequencies frv and frh are values within the range of the threshold values for abnormality determination, and sends the result of the determination to an image generation portion (or image generation circuit) 34d and the driving control portion 34b. The image generation portion 34d superimposes the information regarding the determination result onto an image signal and outputs the resultant signal to the monitor 4. In the case of a determination result indicating the scanning endoscope 2 is normal, the monitor 4 displays information to the effect that the scanning endoscope is normal or that there is no abnormality or the like. In contrast, in the case of a determination result indicating the scanning endoscope 2 is abnormal, the monitor 4 displays information to the effect that the scanning endoscope 2 is abnormal or information prompting the user to exchange the scanning endoscope 2 for another normal scanning endoscope 2 because there is an abnormality or the like. Further, in a case where a normal determination result is received, the driving control portion 34b switches so as to end operation in the determination mode and perform operation in the observation mode.

The scanning endoscope apparatus 1 of the present embodiment includes: the scanning endoscope 2 that has the optical fiber 15 forming a light guide portion for guiding an illuminating light for illuminating the subject 5 and emitting the illuminating light from an emitting end, and the actuator 17 configured to oscillate the emitting end of the light guide portion in accordance with a voltage of a signal applied to the actuator in order to scan the illuminating light over the subject 5; the frequency information storage portion 25a forming a storage portion configured to store in advance, as information regarding a frequency of the signal applied to the actuator 17, information regarding a resonance frequency at a time when the emitting end of the light guide portion is caused to oscillate in a resonant state; the variable-frequency signal generating circuit 41b forming an application portion configured to sequentially apply a plurality of signals having different frequencies to the actuator 17; the current measuring portion 34e forming a signal monitoring portion configured to monitor the plurality of signals that are sequentially applied to the actuator 17; and the determination portion 34g configured to compare information regarding a frequency of a signal when impedance is smallest in a case where the actuator 17 is taken as a load among the plurality of signals monitored by the signal monitoring portion with the information regarding the resonance frequency stored in the storage portion to determine whether or not the scanning endoscope 2 is abnormal.

Next, operations of the present embodiment will be described referring to the flowchart in FIG. 7. When an examination on the subject 5 using the scanning endoscope 2 is performed, the scanning endoscope 2 to be used for the examination is connected to the main body apparatus 3 and a power switch of the main body apparatus 3 is turned on. Thereupon, the controller 34 of the main body apparatus 3 is actuated and reads out a program stored in the memory 35, and refers to parameters of initial settings and the like and starts a predetermined operation.

In this case the controller 34 also performs processing to read out information required for subsequent operations from the memory 25 of the scanning endoscope 2 that is connected to the main body apparatus 3, and store the information in the memory 35 or the like. Note that a configuration may also be adopted in which the controller 34 does not perform such processing, and instead reads out the relevant information from the memory 25 when the information stored in the memory 25 is required.

Figure 9:
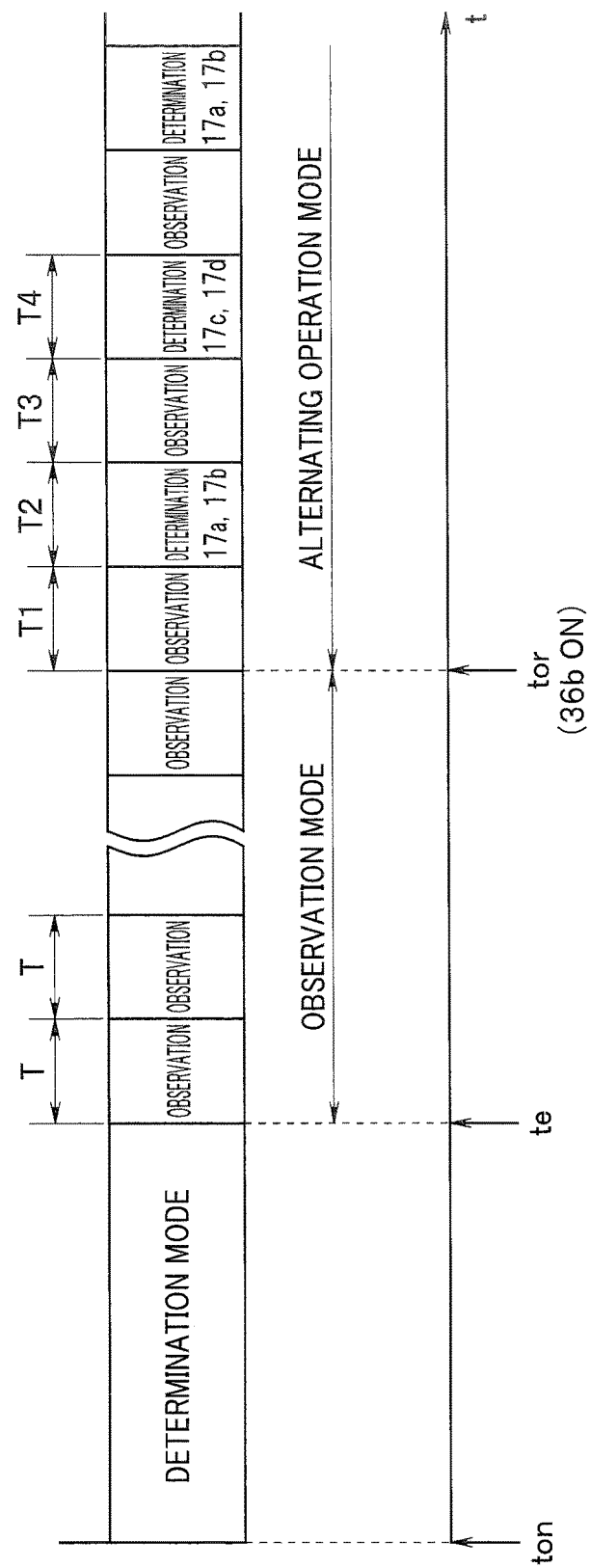
FIG. 9 is an explanatory view for describing operations in an alternating operation mode in FIG. 8.

In the present embodiment an example will be described in which, as a parameters of the initial setting, a parameter is set so as to initially perform the determination mode. In this case, in an initial step S1, the controller 34 controls so as to start operations of the determination mode. Note that FIG. 9 illustrates a time period from a time ton at which the determination mode starts to a time to at which the determination mode ends, and also illustrates a situation in which the alternating operation mode starts after the determination mode.

Upon being activated in the determination mode (upon operations in the determination mode starting), as shown in step S2 the light emission control portion 34a stops a light emission operation of the light source unit 31.

Next, as shown in step S3, the driving control portion 34b controls so that the signal generator 32a outputs a signal for determination in which the frequency varies which is generated by the variable-frequency signal generating circuit 41b to, for example, the actuator elements 17a and 17b that scan in one scanning direction of the actuator 17.

In this case, the driving control portion 34b controls so as to decrease the gain of the amplifier 32d that outputs the signal for determination so that the amplitude of the signal for determination becomes less than the amplitude of a driving signal in the observation mode. That is, the driving control portion 34b controls so as to change the frequency of the signal for determination with a small amplitude and apply the signal for determination to the actuator elements 17a and 17b through the drive wire 18a.

Figure 7:
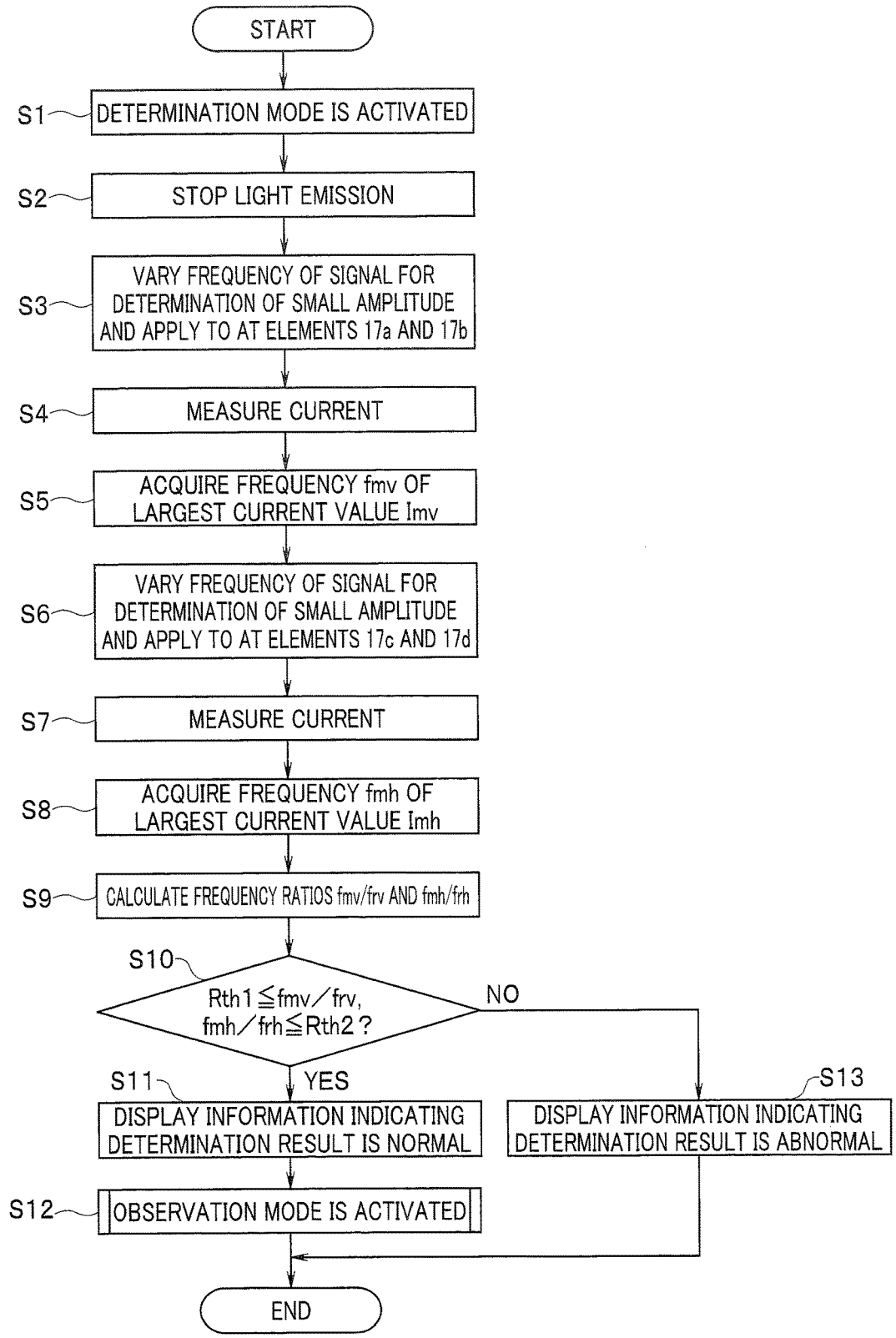
FIG. 7 is a flowchart illustrating processing contents in a determination mode according to a first embodiment.

Note that, in FIG. 7, the actuator elements 17a and 17b are abbreviated as "AT elements 17a and 17b" (the actuator elements 17c and 17d are also abbreviated in a similar manner). In a case where the frequency of the signal for determination with a small amplitude is changed and the signal for determination is applied to the actuator elements 17a and 17b as shown in step S3, the current measuring portion 34e measures the current that flows in the drive wire 18a, as shown in step S4.

Further, as shown in step S5, the current measuring portion 34e acquires the frequency fmv of the signal for determination at a time when the largest current value Imv flows in the drive wire 18a. The current measuring portion 34e sends the acquired frequency fmv to the frequency ratio operation portion 34f. Note that, although in the operations illustrated in FIG. 7 signals for determination with a small amplitude are (temporally) sequentially applied to the one pair of actuator elements 17a and 17c and the other pair of actuator elements 17b and 17d and the largest current values Imv and Imh are sequentially acquired, as described later, a configuration may also be adopted so that signals for determination with a small amplitude can be simultaneously applied to the two pairs of actuator elements 17a and 17c, and 17b and 17d to enable the largest current values Imv and Imh to be sequentially acquired at the same time.

Next, in step S6, in substantially the same manner as in step S3, the driving control portion 34b controls so as to change the frequency of the signal for determination with a small amplitude and apply the signal for determination to the actuator elements 17c and 17d through the drive wire 18b.

Next, in step S7, the current measuring portion 34e measures the current flowing in the drive wire 18b in substantially the same manner as in step S4.

Next, in step S8, in substantially the same manner as in step S5, the current measuring portion 34e acquires the frequency fmh of the signal for determination when the largest current value Imh flows in the drive wire 18b. The current measuring portion 34e sends the acquired frequency fmh to the frequency ratio operation portion 34f.

As shown in the subsequent step S9, the frequency ratio operation portion 34f calculates the frequency ratios Fmv/frv and fmh/frh. The frequency ratio operation portion 34f sends the calculated frequency ratios fmv/frv and fmh/frh to the determination portion 34g.

As shown in the subsequent step S10, the determination portion 34g determines whether or not the frequency ratios fmv/frv and fmh/frh are within the range of the threshold values.

The determination portion 34g determines whether or not the frequency ratio fmv/frv is a value within a range from a lower limit-side threshold value Rth1 to an upper limit-side threshold value Rth2 (that is, whether or not Rth1≤fmv/frv≤Rth2). Likewise, the determination portion 34g determines whether or not the frequency ratio fmh/frh is a value within the range from the lower limit-side threshold value Rth1 to the upper limit-side threshold value Rth2 (that is, whether or not Rth1≤fmh/frh≤Rth2). Note that, in FIG. 7, the contents of the determination by the determination portion 34g are represented using a simplified notation. The determination portion 34g sends the determination result to the image generation portion 34d.

When the result determined by the determination processing in step S10 is that the two frequency ratios fmv/frv and fmh/frh are both within the range of the threshold values, the determination portion 34g determines that the scanning endoscope 2 is normal, and as shown in the subsequent step S11, the image generation portion 34d outputs information for the normal determination result to the monitor 4. The monitor 4 then displays information to the effect that the scanning endoscope 2 is normal. The determination portion 34g also sends information indicating the normal determination result to the driving control portion 34b.

Next, as shown in step S12, the driving control portion 34b controls so as to end the determination mode and initiate the observation mode.

In contrast, if the result of the determination processing in step S10 is that at least one of the two frequency ratios fmv/frv and fmh/frh is not within the range of the threshold values, the determination portion 34g determines that there is an abnormality and, as shown in step S13, the image generation portion 34d outputs information to the effect that the determination result is that the scanning endoscope 2 is abnormal to the monitor 4. The monitor 4 then displays information indicating that the scanning endoscope 2 is abnormal, and thereby ends the processing in FIG. 7. Note that a configuration may also be adopted so that a message prompting the user to exchange the scanning endoscope 2 because of an abnormality is displayed in a case where information indicating that the scanning endoscope 2 is abnormal is displayed in step S13.

Figure 8:
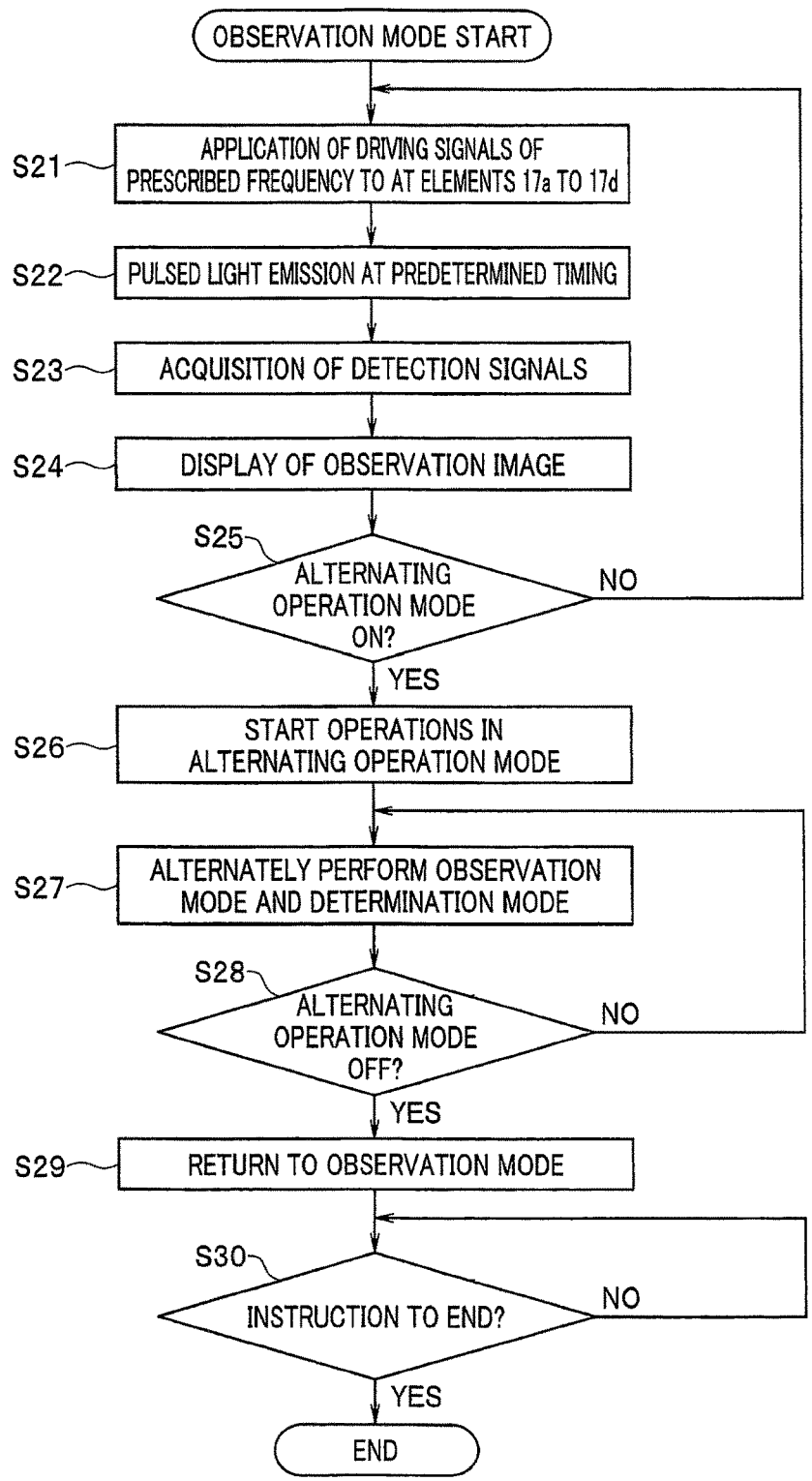
FIG. 8 is a flowchart illustrating processing contents in a case of an observation mode according to the first embodiment.

FIG. 8 illustrates a representative example of the processing contents in a case where the observation mode is initiated (started).

When the observation mode starts, first, in step S21, the driving control portion 34b controls so that the signal generator 32a outputs alternating current signals of prescribed frequencies. The driving signals which are shown in FIG. 3 that have prescribed frequencies which are outputted from the amplifiers 32d and 32e are applied to the actuator elements 17a and 17b and the actuator elements 17c and 17d through the drive wires 18a and 18b.

Further, in step S22 the light emission control portion 34a controls so as to cause the R, G and B light sources 31a to 31c in the light source unit 31 to emit pulsed light at predetermined timings in accordance with information regarding irradiation positions that is stored in the memory 35 (or the memory 25). Illuminating light emitted as the pulsed light is irradiated to the subject 5 side from the distal end face of the optical fiber 15 via the illumination lens 16. That is, during the course of the distal end of the optical fiber 15 two-dimensionally scanning so as to trace a spiral trajectory, pulsed light is emitted sequentially at predetermined timings, and illuminating light that is emitted as the pulsed light is irradiated to (an observation site inside the body cavity on) the subject 5 side.

In this case, the light-receiving optical fibers 23 receive reflected light of the illuminating light irradiated to the subject 5 side, and output the reflected light to the detection unit 33.

Next, as shown in step S23, the detection unit 33 acquires detection signals obtained by subjecting the inputted reflected light to photoelectric conversion, and outputs the detection signals to the image generation portion 34d.

In step S24, in a case where the distal end of the optical fiber 15 scanned spirally, the image generation portion 34d generates an image signal for an observation image based on the detection signals acquired by the detection unit 33 and information regarding irradiation positions stored in the memory 35, and outputs the image signal for an observation image to the monitor 4. The monitor 4 then displays the observation image.

A surgeon diagnoses (examines) the observation site of the subject 5 while observing the observation image displayed on the monitor 4. The surgeon also moves the distal end portion 11 of the insertion portion 6 which is inserted inside the body cavity, to examine the inside of the body cavity that has a luminal shape.

In step S25, the driving control portion 34b monitors an operation performed by the alternating operation mode switch 26b to determine whether or not the alternating operation mode switch 26b is turned on, and if the alternating operation mode switch 26b is not turned on the driving control portion 34b returns to the processing in step S21 to repeat performance of processing in the observation mode. In contrast, if the alternating operation mode switch 26b is turned on, as shown in the next step S26, the controller 34 controls so as to start the alternating operation mode (or interchangingoperation mode) that alternates between operation in the observation mode and operation in the determination mode, for example, every single frame period.

Note that a configuration may also be adopted in which the surgeon turns on the alternating operation mode switch 26b in a case where there is a possibility that the distal end portion 11 of the insertion portion 6 deforms, such as when passing the distal end portion 11 at a slow speed through a luminal site that is narrow and curved.

When the alternating operation mode starts, in step S27, operations are repeated to perform operation in the observation mode and operation in the determination mode alternately for each single frame period.

Next, in step S28, the driving control portion 34b monitors to detect the performance of an operation to turn off the alternating operation mode switch 26b and determine whether or not the alternating operation mode switch 26b is turned off. If the alternating operation mode switch 26b is not turned off, the driving control portion 34b returns to the processing in step S27 and repeatedly performs processing in the alternating operation mode. On the other hand, if the alternating operation mode switch 26b is turned off, as shown in the next step S29, the controller 34 controls so as to return to the observation mode, and controls so as to perform operation in the observation mode.

Next, in step S30, the controller 34 determines whether or not an instruction operation to instruct that the examination be ended was performed at the input portion 36. If the instruction operation to instruct that the examination be ended was not performed, the controller 34 continues operation in the observation mode. In contrast, if the instruction operation to instruct that the examination be ended was performed at the input portion 36, the controller 34 ends the processing in FIG. 8.

Next, operation in the alternating operation mode will be described referring to FIG. 9.

When the alternating operation mode starts (the start time is indicated by for in FIG. 9), the controller 34 controls so as to, for example, operate in the observation mode in a first single frame period T1, and controls so as to operate in the determination mode in the subsequent second single frame period T2. Further, the controller 34 controls so as to operate in the observation mode in a third single frame period T3, and operate in the determination mode in the subsequent fourth single frame period T4. Note that the value of each frame period Ti (i: natural number) is equal to T.

That is, the scanning endoscope 2 operates in the observation mode in odd-numbered frame periods Ti (i=2n−1, where n is a natural number) and operates in the determination mode in even-numbered frame periods Ti (i=2n). Note that a configuration may be adopted so that, when the alternating operation mode starts, in the first single frame period T1, the scanning endoscope 2 operates in the determination mode, or operates in the observation mode as described above and performs processing required for the determination mode during that period and then operates in the determination mode in the following single frame period T2.

Further, in the present embodiment a configuration is adopted so as to alternately drive the actuator elements 17a and 17b and the actuator elements 17c and 17d which oscillate (vibrate) in two orthogonal directions in the determination mode during the even-numbered frame periods Ti (i=2n).

For example, in the second frame period T2 (the driving control portion 34b of) the controller 34 controls so as to apply a signal for determination to the actuator elements 17a and 17b. In this case, the current measuring portion 34e detects the frequency fmv at the time of the largest current value Imv, the frequency ratio operation portion 34f calculates the frequency ratio fmv/frv, and the determination portion 34g makes a determination by comparing the frequency ratio fmv/frv with the threshold values.

FIG. 10 illustrates the determination processing performed by the determination portion 34g. When the determination processing starts, in the initial step S41 the determination portion 34g acquires the frequency ratio fmv/frv calculated by the frequency ratio operation portion 34f. Next, in step S42, the determination portion 34g determines whether a parameter with respect to the alternating operation mode is the default setting or is a parameter selected by means of the parameter selection switch 26c that is different to the default setting.

If the relevant parameter is the default setting, next, in step S43, the determination portion 34g determines whether or not the frequency ratio fmv/frv is within the range formed by the two threshold values Rth1 and Rth2. That is, the determination portion 34g determines whether or not the calculated frequency ratio fmv/frv satisfies the condition Rth1≤fmv/frv≤Rth2.

If the determination result is that the calculated frequency ratio fmv/frv satisfies the condition, as shown in step S44, the determination portion 34g determines that the scanning endoscope 2 is normal. The determination portion 34g sends the determination result to the image generation portion 34d. The image generation portion 34d sends a signal for displaying a determination result that the scanning endoscope 2 is normal to the monitor 4, and as shown in step S45, the monitor 4 displays information to the effect that the scanning endoscope 2 is normal.

In contrast, if the result of the determination in step S43 is that the calculated frequency ratio fmv/frv does not satisfy the condition, as shown in step S46, the determination portion 34g determines that the scanning endoscope 2 is abnormal, and in step S47 the monitor 4 displays information to the effect that the scanning endoscope 2 is abnormal.

On the other hand, in the determination processing in step S42, if the default setting is not set, as shown in step S48, the determination portion 34g performs a determination using threshold values Rth11 (>Rth1) and Rth21 (<Rth2) which are values that are closer to 1 than the threshold values Rth1 and Rth2 in step S10 in FIG. 7. Note that the threshold value information storage portion 25b stores these threshold values Rth11 and Rth21.

If the result of the determination in step S48 is that the calculated frequency ratio fmv/frv satisfies the condition Rth11≤fmv/frv≤Rth21, the determination portion 34g transitions to the processing shown in step S44.

In contrast, if the calculated frequency ratio fmv/frv does not satisfy the condition in step S48, that is, when the determination result is Rth11>fmv/frv or fmv/frv>Rth21, as shown in step S49, the determination portion 34g determines that a characteristic of the actuator elements 17a and 17b changed and that the actuator elements 17a and 17b are in a state in which a characteristic thereof deviates from a normal characteristic.

Further, as shown in step S50, the monitor 4 displays information to the effect that a characteristic of the actuator elements 17a and 17b deviates from the state of a normal characteristic, or that the current state is a state in which the image is degraded or the like, and ends the processing illustrated in FIG. 10.

Substantially the same operation is also performed in the fourth single frame period T4, although the oscillation direction is different (to the case of the single frame period T2 in the above described. That is, almost the same operation is performed except that the aforementioned actuator elements 17a and 17b are replaced with the actuator elements 17c and 17d, and the frequency fmv and the resonance frequency frv are replaced with the frequency fmh and the resonance frequency frh, respectively.

Note that the operations in the observation mode are the same as operations in a single frame period in the operations (steps S21 to 24) in the case of the observation mode that are illustrated in FIG. 8. However, an observation image acquired in the observation mode is held in a frame memory for the next single frame period in the determination mode, and is then displayed on the monitor 4.

According to the first embodiment that operates in this way, an abnormal state of the actuator 17 that is mounted in the scanning endoscope 2 can be simply detected, and the scanning endoscope 2 which is in an abnormal state can be prevented from being used in an examination. That is, before performing endoscopy using the scanning endoscope 2, the resonance frequency is measured and an abnormal state can be simply detected by comparing the measured resonance frequency with information regarding a resonance frequency that is stored in advance in the frequency storage portion in a normal state, and thus performance of endoscopy using the scanning endoscope 2 which is in an abnormal state can be prevented.

Thus, according to the present embodiment, whether or not the actuator 17 is in an abnormal state (faulty state) is determined once in the determination mode (and the determination result is notified) before a time when the power is turned on and endoscopy is performed using the scanning endoscope 2 (before the time to of starting the observation mode in FIG. 9), and hence the performance of an examination using the scanning endoscope 2 in the case where the actuator 17 is in an abnormal state (faulty state) can be prevented.

Further, according to the present embodiment, while the scanning endoscope 2 is being used for endoscopy also, while observation images are acquired it can be determined whether the scanning endoscope 2 is in an abnormal state or in a state that deviates from the normal state which is a state prior to entering an abnormal state.

Note that, in the case of the determination mode, although as shown in FIG. 7 operations are performed in which the variable-frequency signal generating circuit 41b generates signals for determination with a small amplitude in the vertical direction and the horizontal direction in sequence temporally, the respective currents thereof are measured, and frequencies at times when the current values become the largest current values Imv and Imh are sequentially acquired, a configuration may also be adopted in which signals for determination with a small amplitude are generated at the same time, and frequencies at times when the current values become the largest current values Imv and Imh are acquired simultaneously.

Specifically, in the case of the determination mode, in FIG. 5, the variable-frequency signal generating circuit 41b (is configured to) applies a signal for determination with a small amplitude to the contacts b and c of the switching switch circuit 42b. Further, at such a time, a configuration may be adopted so as to measure the currents that flow to the respective pairs of actuator elements 17a and 17c, and 17b and 17d by means of the two current measurement circuits 34ea and 34eb, and simultaneously (in parallel) acquire the frequencies at which the current values become the largest current values Imv and Imh In this case, the serial processing in steps S3 to S8 in FIG. 7 becomes processing in which steps S3 to S5 and steps S6 to S8 are performed in parallel. That is, steps S3 and S6 are simultaneously performed in parallel, then steps S4 and S7 are simultaneously performed in parallel, and next steps S5 and S8 are simultaneously performed in parallel. By adopting this configuration, the processing time in the determination mode can be shortened.

Note that, although in the above described embodiment the signal monitoring portion is constituted by the current measuring portion 34e, the signal monitoring portion may be constituted by a voltage measurement portion (or voltage measurement circuit) that monitors or measures a voltage. For example, reference resistances (taken as R1 and R2) for which the resistance values are small are provided partway along the drive wires 18a and 18b, respectively, the voltages across the resistances R1 and R2 are measured with the voltage measurement portion, and frequencies fmv' and fmh' are acquired at which the largest voltage values are obtained. These frequencies fmv' and fmh' correspond to the frequencies fmv and fmh in the case of the largest current values Imv and Imh. Therefore, the processing after acquisition of the frequencies fmv' and fmh' is similar to the processing after acquisition of the frequencies fmv and fmh. When such a configuration is adopted, the same advantageous effects as in the first embodiment are obtained.

The configuration within the controller 34 in FIG. 1 illustrates one configuration example, and the present invention is not limited to the configuration example illustrated in FIG. 1. For example, the determination portion 34g may be configured to include the function of the frequency ratio operation portion 34f.

Further, the determination portion 34g is not limited to a case of using a frequency ratio to determine whether or not there is an abnormality or the like, and as described above in FIG. 6, for example, the determination portion 34g may be configured to determine whether or not there is an abnormality by comparing an acquired frequency fmv and a frequency deviation amount Δs or the like from the resonance frequency frv (stored in the resonance frequency information storage portion 25b) which corresponds to the relevant frequency. With respect to an acquired frequency fmh also, the determination portion 34g may be configured to similarly determine whether or not there is an abnormality by comparing the acquired frequency fmh with a frequency deviation amount or the like from the resonance frequency frh. Further, as described above, in a case where the values of the two resonance frequencies frv and frh can be approximated as being equal, a configuration may be adopted so as to determine whether or not there is an abnormality or the like using a single resonance frequency or a common resonance frequency.

What is claimed is:

1. A scanning endoscope apparatus comprising:
a scanning endoscope comprising:
   a light guide configured to guide an illuminating light for illuminating a subject and emit the illuminating light from an emitting end; and
   an actuator configured to oscillate the emitting end of the light guide in accordance with a voltage of a signal that is applied to the actuator so that the illuminating light scans over the subject;
a storage configured to store in advance, as information regarding a frequency of the signal that is applied to the actuator, information regarding a resonance frequency at a time when the emitting end of the light guide is caused to oscillate in a resonant state;
a signal generating circuit configured to sequentially apply a plurality of signals having different frequencies to the actuator;
a signal monitoring circuit configured to monitor the plurality of signals that are sequentially applied to the actuator;
a determination circuit configured to compare information regarding a frequency of a signal at a time when an impedance is smallest in a case where the actuator is taken as a load among the plurality of signals monitored by the signal monitoring circuit with the information regarding the resonance frequency stored in the storage to determine whether or not the scanning endoscope is abnormal; and
a mode switching switch configured to switch between an observation mode that obtains an observation image of the subject by means of the scanning endoscope, and a determination mode that determines an abnormality of the scanning endoscope,
wherein, when a mode is switched to the determination mode by the mode switching switch, the signal generating circuit is configured to sequentially apply to the actuator the plurality of signals having different frequencies in which an amplitude is smaller than in a case where a signal of a prescribed frequency is applied to the actuator when in the observation mode.

2. A scanning endoscope apparatus comprising:
a scanning endoscope comprising:
   a light guide configured to guide an illuminating light for illuminating a subject and emit the illuminating light from an emitting end; and
   an actuator configured to oscillate the emitting end of the light guide in accordance with a voltage of a signal that is applied to the actuator so that the illuminating light scans over the subject;
a storage configured to store in advance, as information regarding a frequency of the signal that is applied to the actuator, information regarding a resonance frequency at a time when the emitting end of the light guide is caused to oscillate in a resonant state;
a signal generating circuit configured to sequentially apply a plurality of signals having different frequencies to the actuator;
a signal monitoring circuit configured to monitor the plurality of signals that are sequentially applied to the actuator;

a determination circuit configured to compare information regarding a frequency of a signal at a time when an impedance is smallest in a case where the actuator is taken as a load among the plurality of signals monitored by the signal monitoring circuit with the information regarding the resonance frequency stored in the storage to determine whether or not the scanning endoscope is abnormal; and a switch configured to alternately switch between an observation mode that applies a signal of a prescribed frequency to the actuator and acquires an observation image of the subject by means of the scanning endoscope, and a determination mode that sequentially applies the plurality of signals of different frequencies to the actuator and determines an abnormality of the scanning endoscope by means of the determination circuit.

3. A scanning endoscope apparatus comprising:

a scanning endoscope comprising:

a light guide configured to guide an illuminating light for illuminating a subject and emit the illuminating light from an emitting end; and an actuator configured to oscillate the emitting end of the light guide in accordance with a voltage of a signal that is applied to the actuator so that the illuminating light scans over the subject;

a storage configured to store in advance, as information regarding a frequency of the signal that is applied to the actuator, information regarding a resonance frequency at a time when the emitting end of the light guide is caused to oscillate in a resonant state;

a signal generating circuit configured to sequentially apply a plurality of signals having different frequencies to the actuator;

a signal monitoring circuit configured to monitor the plurality of signals that are sequentially applied to the actuator;

a determination circuit configured to compare information regarding a frequency of a signal at a time when an impedance is smallest in a case where the actuator is taken as a load among the plurality of signals monitored by the signal monitoring circuit with the information regarding the resonance frequency stored in the storage to determine whether or not the scanning endoscope is abnormal;

a light source configured to generate an illuminating light to be supplied to the light guide; and an emission control circuit configured to control emission of the illuminating light, wherein the emission control circuit is configured to control so as not to irradiate the illuminating light at the subject in a case where it is determined by the determination circuit that the scanning endoscope is abnormal.

4. The scanning endoscope apparatus according to claim 1, wherein the signal monitoring circuit is comprised by a current measuring circuit configured to, in a case of monitoring signals at a time when the impedance is smallest in a case where the plurality of signals are sequentially applied when the actuator is taken as a load, measure a current flowing to the actuator through a drive wire that is connected to the actuator, and detect a signal in a case where the current is largest as a signal at the time when the impedance is smallest.

5. The scanning endoscope apparatus according to claim 2, wherein the signal monitoring circuit is comprised by a current measuring circuit configured to, in a case of monitoring signals at a time when the impedance is smallest in a case where the plurality of signals are sequentially applied when the actuator is taken as a load, measure a current flowing to the actuator through a drive wire that is connected to the actuator, and detect a signal in a case where the current is largest as a signal at the time when the impedance is smallest.

6. The scanning endoscope apparatus according to claim 3, wherein the signal monitoring circuit is comprised by a current measuring circuit configured to, in a case of monitoring signals at a time when the impedance is smallest in a case where the plurality of signals are sequentially applied when the actuator is taken as a load, measure a current flowing to the actuator through a drive wire that is connected to the actuator, and detect a signal in a case where the current is largest as a signal at the time when the impedance is smallest.

7. The scanning endoscope apparatus according to claim 1, wherein the actuator comprises a first actuator and a second actuator configured to cause the emitting end of the light guide to oscillate in two orthogonal directions, respectively, and wherein in the determination mode, the signal monitoring circuit is configured to monitor the plurality of signals that are sequentially applied to the first actuator by the signal generation circuit, and then monitor the plurality of signals that are sequentially applied to the second actuator by the signal generating circuit.

8. The scanning endoscope apparatus according to claim 1, further comprising a light source configured to generate an illuminating light to be supplied to the light guide; and a light emission control circuit configured to control emission of the illuminating light, wherein, in the determination mode, the light emission control circuit is configured to control so as to stop emission of the illuminating light.

9. The scanning endoscope apparatus according to claim 1, wherein in a case where the frequency at a time when the impedance is smallest is represented by fm and the resonance frequency is represented by fr, the determination circuit is configured to determine that the scanning endoscope is abnormal when a frequency ratio fm/fr is lower than a first threshold value th1 that is preset as a value that is less than 1 or when the frequency ratio fm/fr is higher than a second threshold value th2 that is preset as a value that is greater than 1, and wherein in a case where the frequency ratio fm/fr is between the first threshold value th1 and the second threshold value th2, the determination circuit is configured to determine that the scanning endoscope is not abnormal.

10. The scanning endoscope apparatus according to claim 2, wherein in a case where the frequency at a time when the impedance is smallest is represented by fm and the resonance frequency is represented by fr, the determination circuit is configured to determine that the scanning endoscope is abnormal when a frequency ratio fm/fr is lower than a first threshold value th1 that is preset as a value that is less than 1 or when the frequency ratio fm/fr is higher than a second threshold value th2 that is preset as a value that is greater than 1, and wherein in a case where the frequency ratio fm/fr is between the first threshold value th1 and the second threshold value th2, the determination circuit is configured to determine that the scanning endoscope is not abnormal.

11. The scanning endoscope apparatus according to claim 3, wherein in a case where the frequency at a time when the impedance is smallest is represented by fm and the resonance frequency is represented by fr, the determination circuit is configured to determine that the scanning endoscope is abnormal when a frequency ratio fm/fr is lower than a first threshold value th1 that is preset as a value that is less than 1 or when the frequency ratio fm/fr is higher than a second threshold value th2 that is preset as a value that is greater than 1, and wherein in a case where the frequency ratio fm/fr is between the first threshold value th1 and the second threshold value th2, the determination circuit is configured to determine that the scanning endoscope is not abnormal.

12. The scanning endoscope apparatus according to claim 1, wherein the actuator is comprised by two actuators configured to cause the emitting end of the light guide to oscillate in two orthogonal directions, respectively, and wherein in a case where a mode is switched to a switching mode that alternately performs an operation in the observation mode and an operation in the determination mode,
a determination as to whether or not the scanning endoscope is abnormal is made by alternately using the two actuator so as to perform the operation in the determination mode using one of the two actuator in a next single frame period after a single frame period in the observation mode, and to perform the operation in the determination mode using the other of the two actuator in a single frame period that is after a next single frame period in the observation mode.

13. The scanning endoscope apparatus according to claim 2, wherein in the determination mode, in a case where the frequency at a time when the impedance is smallest is represented by fm and the resonance frequency is represented by fr, the determination circuit is configured to determine that the scanning endoscope is abnormal when a frequency ratio fm/fr is lower than a first threshold value th1 that is preset as a value that is less than 1 or when the frequency ratio fm/fr is higher than a second threshold value th2 that is preset as a value that is greater than 1, and wherein in a case where the frequency ratio fm/fr is between the first threshold value th1 and the second threshold value th2, the determination circuit is configured to determine that the scanning endoscope is not abnormal.

14. The scanning endoscope apparatus according to claim 13, wherein the storage is configured to store a third threshold value th3 that is set to a value between the first threshold value th1 and 1, and a fourth threshold value th4 that is set to a value between 1 and the second threshold value th2, and wherein in the determination mode, in a case where the frequency fm is lower than the third threshold value th3 or a case where the frequency fm is greater than the fourth threshold value th4, the determination circuit is configured to determine that the scanning endoscope deviates from a normal state.

15. The scanning endoscope apparatus according to claim 1, wherein the signal monitoring circuit is configured to measure a current value corresponding to the plurality of signals that are sequentially applied to the actuator, and wherein the determination circuit is configured to determine whether or not the scanning endoscope is abnormal by comparing information regarding a frequency of a signal in a case where the current value is largest among the plurality of signals with information regarding the resonance frequency.

16. The scanning endoscope apparatus according to claim 2, wherein the signal monitoring circuit is configured to measure a current value corresponding to the plurality of signals that are sequentially applied to the actuator, and wherein the determination circuit is configured to determine whether or not the scanning endoscope is abnormal by comparing information regarding a frequency of a signal in a case where the current value is largest among the plurality of signals with information regarding the resonance frequency.

17. The scanning endoscope apparatus according to claim 3, wherein the signal monitoring circuit is configured to measure a current value corresponding to the plurality of signals that are sequentially applied to the actuator, and wherein the determination circuit is configured to determine whether or not the scanning endoscope is abnormal by comparing information regarding a frequency of a signal in a case where the current value is largest among the plurality of signals with information regarding the resonance frequency.

* * * * *